US010023608B1

(12) United States Patent
Ma et al.

(10) Patent No.: US 10,023,608 B1
(45) Date of Patent: Jul. 17, 2018

(54) PROTEIN PURIFICATION METHODS TO REMOVE IMPURITIES

(71) Applicant: AMGEN INC., Thousand Oaks, CA (US)

(72) Inventors: Junfen Ma, Thousand Oaks, CA (US); Xiaoyang Zhao, Moorpark, CA (US); Brian Williamson, Camarillo, CA (US)

(73) Assignee: AMGEN INC., Thousand Oaks, CA (US)

( * ) Notice: Subject to any disclaimer, the term of this patent is extended or adjusted under 35 U.S.C. 154(b) by 247 days.

(21) Appl. No.: 14/208,043

(22) Filed: Mar. 13, 2014

Related U.S. Application Data

(60) Provisional application No. 61/780,243, filed on Mar. 13, 2013.

(51) Int. Cl.
*C07K 1/20* (2006.01)
*C07K 16/24* (2006.01)
*C07K 19/00* (2006.01)
*C07K 1/16* (2006.01)

(52) U.S. Cl.
CPC ............ *C07K 1/20* (2013.01); *C07K 16/241* (2013.01); *C07K 2317/21* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 4,816,397 A | 3/1989 | Boss et al. | |
| 4,816,567 A | 3/1989 | Cabilly et al. | |
| 4,968,607 A | 11/1990 | Dower et al. | |
| 5,110,913 A | 5/1992 | Coan et al. | |
| 5,118,796 A | 6/1992 | Prior et al. | |
| 5,169,936 A | 12/1992 | Staples et al. | |
| 5,225,539 A | 7/1993 | Winter | |
| 5,429,746 A | 7/1995 | Shadle et al. | |
| 5,641,870 A | 6/1997 | Rinderknecht et al. | |
| 5,767,064 A | 6/1998 | Sims et al. | |
| 5,856,296 A | 1/1999 | Mosley et al. | |
| 5,945,520 A | 8/1999 | Burton et al. | |
| 6,005,082 A | 12/1999 | Smeds | |
| 6,087,329 A | 7/2000 | Armitage et al. | |
| 6,090,382 A | 7/2000 | Salfeld et al. | |
| 6,271,349 B1 | 8/2001 | Dougall et al. | |
| 6,498,236 B1 | 12/2002 | Lihme et al. | |
| 6,870,034 B2 | 3/2005 | Breece et al. | |
| 7,001,550 B2 | 2/2006 | van Reis | |
| 7,008,542 B2 | 3/2006 | Belew et al. | |
| 7,122,641 B2 | 10/2006 | Vedantham et al. | |
| 7,323,553 B2 | 1/2008 | Fahrner et al. | |
| 7,427,659 B2 | 9/2008 | Shukla et al. | |
| 7,714,112 B2 * | 5/2010 | Engstrand ............ | B01D 15/327 530/390.5 |
| 7,750,129 B2 | 7/2010 | Johansson et al. | |
| 7,863,426 B2 | 1/2011 | Wan et al. | |
| 8,063,189 B2 | 11/2011 | Arunakumari et al. | |
| 8,067,182 B2 | 11/2011 | Kelley et al. | |
| 8,231,876 B2 | 7/2012 | Wan et al. | |
| 8,273,707 B2 | 9/2012 | Senczuk et al. | |
| 8,399,627 B2 | 3/2013 | Votsmeier et al. | |
| 8,946,395 B1 | 2/2015 | Herigstad et al. | |
| 8,969,024 B2 | 3/2015 | Kaymakcalan et al. | |
| 9,109,010 B2 | 8/2015 | Hickman et al. | |
| 9,144,755 B2 | 9/2015 | Brown et al. | |
| 9,249,182 B2 * | 2/2016 | Herigstad ............... | C07K 16/00 |
| 9,708,365 B2 | 7/2017 | Mendiratta et al. | |
| 2001/0021525 A1 | 9/2001 | Hirai et al. | |
| 2003/0229212 A1 | 12/2003 | Fahrner et al. | |
| 2004/0162414 A1 | 8/2004 | Santora et al. | |
| 2005/0271654 A1 | 12/2005 | Rinderknecht et al. | |
| 2006/0287432 A1 | 12/2006 | Christensen et al. | |
| 2007/0054390 A1 | 3/2007 | Kelley et al. | |
| 2007/0213513 A1 | 9/2007 | Van Alstine et al. | |
| 2007/0292442 A1 * | 12/2007 | Wan ......................... | C07K 1/18 424/176.1 |
| 2008/0058507 A1 | 3/2008 | Liu et al. | |
| 2009/0247735 A1 * | 10/2009 | Gagnon ................... | C07K 1/165 530/413 |
| 2010/0004907 A1 | 1/2010 | Kidal et al. | |
| 2010/0069617 A1 | 3/2010 | Gagnon | |

(Continued)

FOREIGN PATENT DOCUMENTS

| | | |
|---|---|---|
| EP | 0120694 A2 | 10/1984 |
| EP | 0125023 A1 | 11/1984 |

(Continued)

OTHER PUBLICATIONS

"Optimization of loading conditions on Capto adhere using design of experiments", GE Healthcare Application Note: 28/9078-89 AA (2007).
Bachmann et al., The influence of antigen organization on B cell responsiveness, Science, 262(5138):1448-51 (1993).
Brasel et al., Hematologic effects of flt3 ligand in vivo in mice, Blood, 88(6):2004-12 (1996).
Chaudhary et al., A recombinant immunotoxin consisting of two antibody variable domains fused to Pseudomonas exotoxin, Nature, 339(6223):394-7 (1989).
Chen et al., The distinctive separation attributes of mixed-mode resins and their application in monoclonal antibody downstream purification process, J. Chromatography A, 1217:216-24 (2010).
Eriksson et al., MAb contaminant removal with a multimodal anion exchanger, BioProcess International, 7(2):52-6 (2009).
Fausnaugh et al., Solute and mobile phase contributions to retention in hydrophobic interaction chromatography of proteins, J. Chromatogr., 359:131-46 (1986).

(Continued)

*Primary Examiner* — Daniel E Kolker
*Assistant Examiner* — James Rogers
(74) *Attorney, Agent, or Firm* — Marshall, Gerstein & Borun LLP

(57) ABSTRACT

Disclosed are methods of purifying a protein sample. More specifically, provide are methods of removing or reducing the amount of high molecular weight species and/or high mannose species from a protein sample using a mixed mode chromatography step and a hydrophobic interaction chromatography step.

22 Claims, No Drawings

(56) References Cited

U.S. PATENT DOCUMENTS

| | | |
|---|---|---|
| 2010/0135987 A1 | 6/2010 | Hickman et al. |
| 2010/0145029 A1 | 6/2010 | Gagnon |
| 2011/0002935 A1 | 1/2011 | Wan et al. |
| 2011/0129468 A1 | 6/2011 | Mccue et al. |
| 2011/0130544 A1 | 6/2011 | Ram et al. |
| 2011/0301342 A1 | 12/2011 | Wang et al. |
| 2012/0122076 A1 | 5/2012 | Lau et al. |
| 2012/0122759 A1 | 5/2012 | Brown et al. |
| 2012/0202974 A1 | 8/2012 | Duval et al. |
| 2012/0238730 A1 | 9/2012 | Dong et al. |
| 2012/0264920 A1 | 10/2012 | Wang et al. |
| 2013/0245139 A1 | 9/2013 | Kozlov et al. |
| 2013/0338344 A1 | 12/2013 | Ramasubramanyan et al. |
| 2014/0288272 A1 | 9/2014 | Allison et al. |
| 2014/0288278 A1* | 9/2014 | Nti-Gyabaah ..... B01D 15/3809 530/388.24 |
| 2015/0197579 A1 | 7/2015 | Stefan et al. |
| 2016/0002414 A1 | 1/2016 | Beardmore et al. |
| 2016/0272674 A1 | 9/2016 | Althouse et al. |
| 2016/0347833 A1 | 12/2016 | Jensen et al. |

FOREIGN PATENT DOCUMENTS

| | | |
|---|---|---|
| EP | 0367566 A1 | 5/1990 |
| EP | 0451216 A1 | 10/1991 |
| EP | 0460846 A1 | 12/1991 |
| EP | 0 519 596 A1 | 12/1992 |
| EP | 1308455 | 5/2003 |
| WO | WO-86/01533 A1 | 3/1986 |
| WO | WO-93/08207 A1 | 4/1993 |
| WO | WO-94/28391 A1 | 12/1994 |
| WO | WO-96/33208 A1 | 10/1996 |
| WO | WO-96/40918 A2 | 12/1996 |
| WO | WO-97/01633 A1 | 1/1997 |
| WO | WO-99/57134 A1 | 11/1999 |
| WO | WO-03/102132 A2 | 12/2003 |
| WO | WO-2004/026891 A2 | 4/2004 |
| WO | WO-2006/099308 A2 | 9/2006 |
| WO | WO-2006/110277 A1 | 10/2006 |
| WO | WO-2007/005786 A2 | 1/2007 |
| WO | WO-2007/036745 A2 | 4/2007 |
| WO | WO-2007/117490 A2 | 10/2007 |
| WO | WO-2010/048192 A2 | 4/2010 |
| WO | WO-2010/080062 A1 | 7/2010 |
| WO | WO-2010/102114 A1 | 9/2010 |
| WO | WO-2010/141039 | 12/2010 |
| WO | WO-2011/009623 A1 | 1/2011 |
| WO | WO-2011/073235 A1 | 6/2011 |
| WO | WO-2011/090719 A2 | 7/2011 |
| WO | WO-2011/146179 A2 | 11/2011 |
| WO | WO-2012/014183 A1 | 2/2012 |
| WO | WO-2012/030512 A1 | 3/2012 |
| WO | WO-2012/051147 A1 | 4/2012 |
| WO | WO-2012/068134 A1 | 5/2012 |
| WO | WO-2012/078376 A1 | 6/2012 |
| WO | WO-2013/066707 A1 | 5/2013 |
| WO | WO-2013/067301 A1 | 5/2013 |
| WO | WO-2013/176754 A1 | 11/2013 |
| WO | WO-2014/143185 A1 | 9/2014 |
| WO | WO-2014/145208 A1 | 9/2014 |
| WO | WO-2015/207763 A1 | 12/2014 |
| WO | WO-2015/004679 A1 | 1/2015 |
| WO | WO-2015/070068 A1 | 5/2015 |

OTHER PUBLICATIONS

Goetze et al., High-mannose glycans on the Fc region of therapeutic IgG antibodies increase serum clearance in humans, Glycobiology, 21(7):949-59 (2011).
Guidance for Industry Immunogenicity Assessment for Therapeutic Protein Products, Draft Guidance, U.S. Department of Health and Human Services, Food and Drug Administration, Center for Drug Evaluation and Research and Center for Biologics Evaluation and Research (Feb. 2013).
Kaufman et al., Synthesis, processing, and secretion of recombinant human factor VIII expressed in mammalian cells, J. Biol. Chem., 263(13):6352-62 (1988).
Kaufman,Selection and coamplification of heterologous genes in mammalian cells, Methods Enzymol., 185:537-66 (1990).
Larrick et al., Polymerase chain reaction using mixed primers: cloning of human monoclonal antibody variable region genes from single hybridoma cells, Bio/Technology, 7:934-8 (1989).
McKinnon et al., Expression, purification and characterization of secreted recombinant human insulin-like growth factor-I (IGF-I) and the potent variant des(1-3) IGF-I in Chinese hamster ovary cells, J. Mol. Endocrinol., 6(3):231-9 (1991).
Nau, Effects of mobile phase conditions on protein conformation and chromatographic selectivity in ion exchange and hydrophotobic interaction chromatography, BioChromatography, 4(2):62-8 (1989).
Nau, The role of hydrophobic interaction chromatography in antibody purification—optimization of mobile phase conditions, BioChromatography, 62(5):62-74 (1990).
Pahlman et al., Hydrophobic interaction chromatography on uncharged Sepharose derivatives. Effects of neutral salts on the adsorption of proteins, J. Chromatogr., 131:99-108 (1977).
Porath, Metal Ion—Hydrophobic, Thiophilic and II-Electron Governed Interactions and their Application to Salt-Promoted Protein Adsorption Chromatography, Biotechnol. Prog., 3(1):14-21 (1987).
Queiroz et al., Hydrophobic interaction chromatography of proteins, J. Biotechnol., 87(2):143-59 (2001).
Riechmann et al., Reshaping human antibodies for therapy, Nature, 332(6162):323-7 (1988).
Roberts et al., Generation of an antibody with enhanced affinity and specificity for its antigen by protein engineering, Nature, 328(6132):731-4 (1987).
Roe et al., Protein Purification Methods: A Practical Approach, IRL Press Oxford, pp. 221-232 (1989).
Rosenberg, Effects of protein aggregates: an immunologic perspective, AAPS J., 8(3):E501-7 (2006).
Singleton et al., Cloning and analysis of a Candida albicans gene that affects cell surface hydrophobicity, J. Bacteriol., 183(12):3582-8 (2001).
Urlaub et al., Isolation of Chinese hamster cell mutants deficient in dihydrofolate reductase activity, Proc. Natl. Acad. Sci. USA, 77(7):4216-20 (1980).
Verhoeyen et al., Reshaping human antibodies: grafting an antilysozyme activity, Science, 239(4847):1534-6 (1988).
Wood et al., High level synthesis of immunoglobulins in Chinese hamster ovary cells, J. Immunol., 145(9):3011-6 (1990).
Amersham Biosciences, Antibody Purification Handbook (2002).
Avgerinos G. Abstracts—Extended Reports from the 3rd International Symposium on Downstream Processing of Genetically Engineered Antibodies and Related Molecules, Nice, France, p. 15-16. (2004).
Coffman et al., High-Throughput Screening of Chromatographic Separations: 1. Method Development and Column Modeling, Biotechnology & Bioengineering, 100:605-18 (2008).
Emea, Avastin Scientific Discussion (2005). ("EMEA Avastin").
Fahrner et al., Industrial Purification of Pharmaceutical Antibodies: Development, Operation, and Validation of Chromatography Processes, Biotechnology & Genetic Engineering Reviews, 18:301-27 (2001).
Follman et al., Factorial screening of antibody purification processes using three chromatography steps without protein A, J. Chromatography A, 1024:79-85 (2004).
Gagnon et al., Technology trends in antibody purification, J. Chromatography A., 1221:57-70 (2011).
Gatto, Biologics Targeted at TNF: Design, Production, and Challenges, Reumatismo, 58:94-103 (2006).
Goswami et al., Developments and Challenges for mAb-Based Therapeutics, Antibodies, 2:452-500 (2013).
Graf et al., Ion exchange resins for the purification of monoclonal antibodies from animal cell culture, Bioseparation, 4:7-20 (1994).

(56) References Cited

OTHER PUBLICATIONS

Guidance for Industry—Q6B Specifications: Test Procedures and Acceptance Criteria for Biotechnological / Biological Products, (1999).
Guse et al., Purification and analytical characterization of an anti-CD4 monoclonal antibody for human therapy, *J. of Chromatography A*, 661:13-23 (1994).
Harris et al., Current Trends in Monoclonal Antibody Development and Manufacturing, 12:193-205 (2010).
Jacob et al., Scale-up of Antibody Purification, *Antibodies*, vol. 1: Production & Purification, (2004).
Kelley et al., Downstream Processing of Monoclonal Antibodies: Current Practices and Future Opportunities, Process Scale Purification of Antibodies (2009).
Kramarczyk et al., High-Throughput Screening of Chromatographic Separations: II. *Hydrophobic Interaction*, 100:708-20 (2008).
Lain et al., Development of a High-Capacity MAb Capture Step Based on Cation-Exchange Chromatography, *BioProcess Int'l*, 7:26-34 (2009).
Li et al., Current Therapeutic Antibody Production and Process Optimization, *BioProcessing J.*, 1-8 (2005).
Lienqueo et al., Mathematical correlations for predicating protein retention times in hydrophobic interaction chromatography, 978:71-9 (2002).
Liu et al., Recovery and purification process development for monoclonal antibody production, *mAbs*, 2:480-99 (2010).
Lu et al., Recent Advancement in Application of Hydrophobic Interaction Chromatography for Aggregate Removal in Industrial Purification Process, 10:427-33 (2009).
Luksa et al., Purification of human tumor necrosis factor by membrane chromatography, *J. Chromatography A*, 661:161-8 (1994).
McCue et al., Effect of phenyl sepharose ligand density on protein monomer/aggregate purification and separation using hydrophobic interaction chromatography, *J. Chromatography A*, 1216:209-909 (2009).
Mehta et al., Purifying Therapeutic Monoclonal Antibodies, *SBE Special Section- Bioprocessing*, S14-20 (2008).
Muller-Spath et al., Chromatographic Separation of Three Monoclonal Antibody Variants Using Multicolumn Countercurrent Solvent Gradient Purification (MCSGP), *Biotechnology & Bioengineering*, 100:1166-77 (2008).
Rao et al., Separation of Monoclonal Antibodies by Weak Cation-Exchange Chromatography Using ProPac and ProSwift Columns, Dionex (2010).
Santora et al., Characterization of Noncovalent Complexes of Recombinant Human Monoclonal Antibody and Antigen Using Cation Exchange, Size Exclusion Chromatography, and BIACore, *Analytical Biochem*, 299:119-29 (2001).
Santora et al., Characterization of Recombinant Human Monoclonal Tissue Necrosis Factor-α Antibody Using Cation-Exchange HPLC and Capillary Isoelectric Focusing, *Analytical Biochem.*, 275:98-108 (1999).
Shukla et al., Downstream processing of monoclonal antibodies—Application of platform approaches, *J. Chromatography B.*, 848:28-39 (2006).
Shukla et al., Process Scale Bioseparations for the Biopharmaceutical Industry, Taylor and Francis Group, (2006).
Shukla et al., Recent advances in large-scale production of monoclonal antibodies and related proteins, *Cell Review*, 28:253-61 (2010).
Shukla et al., Strategies to Address Aggregation During Protein A Chromatography, *BioProcess Int'l*, 3:36-45 (2005).
To et al., Hydrophobic interaction chromatography of proteins: I. The effects of protein and adsorbent properties on retention and recovery, *J. Chromatography A*, 1141:191-205 (2007).
Tugcu et al., Maximizing Productivity of Chromatography Steps for Purification of Monoclonal Antibodies, 99( 3):599-613 (2007).
Turner, Manufacturing Process Development and Comparability Studies for Humira, bioLOGIC (2003), Boston, MA (Presentation Slides).
Wan, Process Mapping—A Necessary Step in Product Lifecycle, BioProcess International Conference (2004).
Zhang et al., Isolation and characterization of therapeutic antibody charge variants using cation exchange displacement chromatography, *J. Chromatography A.*, 1218:5079-86 (2011).
Zhou, Implementation of Advanced Technologies in Commercial Monoclonal Antibody Production, *Biotech. J.*, 3:1185-200 (2008).

\* cited by examiner

PROTEIN PURIFICATION METHODS TO REMOVE IMPURITIES

CROSS REFERENCE TO RELATED APPLICATIONS

The benefit of U.S. Application No. 61/780,243, filed Mar. 13, 2013 is claimed, the disclosure of which is incorporated by reference in its entirety.

FIELD OF THE DISCLOSURE

The present disclosure is directed to removal or decrease in amount of high molecular weight species and/or high mannose species from a protein sample using a purification comprising a mixed mode chromatography step and a hydrophobic interaction chromatography step.

BACKGROUND

The purification of proteins for the production of biological or pharmaceutical products from various source materials involves a number of procedures. Therapeutic proteins may be obtained from plasma or tissue extracts, for example, or may be produced by recombinant methods such as by cultures of eukaryotic or prokaryotic cells containing at least one recombinant plasmid encoding the desired protein. The recombinant proteins are then either secreted into the surrounding media or into the perinuclear space, or made intracellularly and extracted from the cells. A number of well-known technologies are utilized for purifying desired proteins from their source material. Purification processes include procedures in which the protein of interest is separated from the source materials on the basis of solubility, ionic charge, molecular size, adsorption properties, and specific binding to other molecules.

When developing processes for commercial production of therapeutically important proteins, purification of the protein sample to remove undesired species in an efficient manner is highly desirable. The present invention provides a purification method for removal of high molecular weight species from a protein sample using two sequential chromatographic steps.

SUMMARY

Provided herein are methods of reducing high molecular weight (HMW) species and/or high mannose species in a protein sample. More specifically, provided are methods of reducing high molecular weight (HMW) species in a protein sample a comprising: (a) subjecting the starting solution having a desired protein to mixed mode chromatography (MMC) to form a first eluate; and (b) subjecting the first eluate to hydrophobic interaction chromatography (HIC) to form a second eluate, wherein the second eluate has fewer or a lower amount of HMW species than the starting solution. In some embodiments, the HIC step is performed before the MMC step. In various embodiments, the methods provided herein do not comprise a separate cation exchange chromatography step and/or a separate anion exchange chromatography step.

In any of the methods of the invention, the MMC step can be performed in bind/elute or flow through mode. The MMC resin can be, for example, Capto® MMC, HEA HyperCel™, PPA HyperCel™, MBI HyperCel™, MEP HyperCel™, Blue Trisacryl M, CFT™ Ceramic Fluoroapatite, CHT™ Ceramic Hydroxyapatite, or ABx resin. In some embodiments, the MMC resin is Capto® Adhere.

In any of the methods of the invention, the HIC step can be performed in bind/elute of flow through mode. The HIC resin can be, for example, Phenyl Sepharose®, Phenyl Sepharose® 6 Fast Flow, Phenyl Sepharose® High Performance, Octyl Sepharose™ High Performance, Fractogel™ EMD Propyl, Fractogel™ EMD Phenyl, Macro-Prep™ Methyl, Macro-Prep™ t-Butyl, WP HI-Propyl ($C_3$)™, Toyopearl™ ether, Toyopearl™ phenyl or Toyopearl™ butyl, or a combination thereof. In some embodiments, the HIC step is performed using Tosoh Phenyl 650S, Tosoh Butyl 650S, Tosoh Hexyl 650C, GE Butyl High Performance, or a SEPHAROSE™ column such as Phenyl SEPHAROSE™ (Pharmacia LCK Biotechnology, AB, Sweden); GE Phenyl 6 Fast Flow High Sub, GE Phenyl 6 Fast Flow Low Sub, GE Butyl 4 Fast Flow, EMD Phenyl columns (E. Merck, Germany); Phenyl HP column (GE Healthcare Life Sciences); MACRO-PREP™ Methyl or MACRO-PREP™ t-Butyl Supports (Bio-Rad, Calif.); WP HI-Propyl (C3)™ column (J. T. Baker, N.J.); and TOYOPEARL™ ether, phenyl or butyl columns (TosoHaas, Pa.). In various cases, the HIC resin is selected from GE Phenyl High Performance; GE Octyl 4 Fast Flow; EMD Fractogel Phenyl; Tosoh Phenyl 650S; Tosoh Butyl 650S; Tosoh Hexyl 650C; GE Butyl High Performance; GE Phenyl 6 Fast Flow High Sub; GE Phenyl 6 Fast Flow Low Sub; GE Butyl 4 Fast Flow; and GE Butyl-6 Fast Flow, or Octyl SEPHAROSE™ High Performance column (Pharmacia LKB Biotechnology, AB, Sweden), FAST FLOW™ column with low or high substitution (Pharmacia LKB Biotechnology, AB, Sweden) as the resin. In some embodiments, the HIC resin is Phenyl HP resin.

In various cases, the HMW species in the second eluate of any of the methods of the invention are 1% or less, 0.5% or less, or 0.2% or less, in each case measured by % by weight. In some cases, the high mannose species in the second eluate of any of the methods of the invention are reduced by about 5% or more, about 10% or more, or about 20% or more, compared to the amount of high mannose species in the starting protein sample.

The protein subjected to any of the methods as disclosed herein can comprise a recombinantly produced protein or polypeptide. In some cases, the protein can be from a cell supernatant or a cell culture harvest, such as from CHO cells. The protein can be an antibody, such as an IgG1 or an IgG2 antibody. The antibody can be a monoclonal antibody, and in some cases, can be a human antibody. In specific embodiments, the antibody is a IgG1 antibody. The antibody can be an antibody that, e.g., specifically binds to TNFα, such as infliximab, adalimumab, certolizumab pegol, or golimumab. In some embodiments, the antibody is adalimumab or a biosimilar or bioequivalent thereof.

Another aspect provided herein are methods of reducing high molecular weight (HMW) species in a sample comprising adalimumab or a biosimilar thereof comprising (a) subjecting the sample to mixed mode chromatography (MMC) in flow through mode to form a first eluate; and (b) subjecting the first eluate to hydrophobic interaction chromatography (HIC) in bind/elute mode to form a second eluate, wherein the second elute has fewer HMW species than the sample. In various embodiments, the method further provides fewer high mannose species in the second eluate than in the sample. In some embodiments, the amount of HMW species in the second eluate is 1% by weight or less, or 0.5% by weight or less, or 0.2% by weight or less. In various embodiments, the amount of high mannose species in the second eluate decreases by 10% or more or 20% or more, compared to the amount of high mannose species in the sample.

In various embodiments of the methods disclosed herein, the MMC step is performed using Capto® Adhere resin in flow through mode. The Capto® Adhere resin can have a protein loading of about 30 to about 120 g/L. For the MMC step, the sample can be conditioned prior to loading onto the MMC column to have a conductivity of about 15 to about 19 mS/cm and a pH of about 6.9 to about 7.3. The sample can be loaded onto the MMC column using a loading buffer. In some embodiments, the MMC column can be equilibrated prior to sample loading using an equilibration buffer. The equilibration buffer can be at a conductivity of about 15 to about 19 mS/cm and a pH of about 7 to about 7.5. In various embodiments, the MMC column can be washed with a washing buffer. The washing buffer can be at a conductivity of about 15 to about 19 mS/cm and a pH of about 7 to about 7.5. The MMC step can be performed once, twice, or three times, and in some specific embodiments, is performed twice. In various embodiments, at least one of the loading buffer, equilibration buffer, and washing buffer is at a pH of about 7 to 7.2 and comprises (a) 116 mM NaCl, 100 mM Tris-HCl; (b) 85 mM NaCl, 150 mM Tris-HCl; (c) 169 mM NaCl, 25 mM HEPES; (d) 169 mM NaCl, 25 mM MOPS; or (e) 184 mM NaCl, 100 mM MOPS. In various embodiments, the MMC step can be performed at a linear velocity of about 100 to about 300 cm/hr.

In various embodiments of the methods disclosed herein, the HIC step can be performed using Phenyl HP resin in bind/elute mode. The HIC column can be equilibrated prior to protein loading using an equilibration buffer. In some embodiments, the equilibration buffer comprises 20 mM MOPS and 1.1 M kosmotropic salt and is at a pH of about 5 to about 8. In various embodiments, the kosmotropic salt comprises one or more of ammonium sulfate, sodium sulfate, potassium sulfate, or sodium citrate. In some embodiments, the column is washed with a washing buffer after the protein is loaded onto the column. In some cases, the washing buffer comprises 20 mM MOPS and 1.1 M kosmotropic salt and is at a pH of about 5 to about 8, and in some cases the kosmotropic salt comprises one or more of ammonium sulfate, sodium sulfate, potassium sulfate, or sodium citrate. In various embodiments, the protein (e.g., adalimumab) is eluted from the column using an eluting buffer on a gradient from 0-100%, e.g., over 10-20 column volumes. In some embodiments, the eluting buffer has the same pH and buffer species as the washing buffer but does not comprise a kosmotropic salt. In some embodiments, the eluting buffer comprises 20 mM MOPS.

DETAILED DESCRIPTION

The methods disclosed herein are directed to removing high molecular weight ("HMW") species and/or high mannose species from a protein sample (alternatively referred to as protein preparation throughout). High molecular weight species may include dimers, trimers, or aggregates of a desired protein, as well as undesired polypeptide contaminants. Such HMW species or protein aggregates can be present in the preparation of polypeptides expressed by a host cell and may contribute to increased immunogenicity if present in the drug product administered to a patient. Although definitive information is lacking regarding the types and quantities of aggregates needed to generate immune responses for any given therapeutic protein product, it is generally recognized that higher molecular weight aggregates (e.g., with a molecular weight greater than 100 kD) and particles are more potent in eliciting such responses than lower molecular weight aggregates (see, e.g., Bachmann, et al., 1993, Science, 262: 1448-51; and Rosenberg, A. S., The AAPS Journal, 2006; 8(3), Article 59).

The methods disclosed herein can alternatively or additionally result in a reduction of high mannose glycoforms or high mannose glycans, alternatively referred to as high mannose species throughout. High mannose species contain unsubstituted terminal mannose sugars and typically contain between five and nine mannose residues attached to the chitobiose (GlcNAc2) core, e.g. high mannose-3 (man-3), high mannose-5 (man-5) and high-mannose-9 (man-9). The name abbreviations are indicative of the total number of mannose residues in the structure. Therapeutic IgGs containing high-mannose glycans are cleared more rapidly in humans than other glycan forms (Goetze, A. M., et al., 2011, Glycobiology vol. 21(7), pp. 949-959). Reducing the high mannose content of therapeutic antibodies may therefore be desirable in order to increase the half-life of such antibodies in circulation.

Mixed Mode Chromatography

Mixed mode chromatography (MMC) refers to chromatography that substantially involves a combination of two or more chemical interactions within in a solid support. Examples of chemical interactions that can be combined in mixed mode supports include but are not limited to cation exchange, anion exchange, hydrophobic interaction, hydrophilic interaction, hydrogen bonding, pi-pi bonding, and metal affinity.

The MMC contains a solid or stationary phase or resin (immobilized hydrophobic groups on the matrix) and a soluble mobile or solution phase (containing proteins) in which the chemical interactions between a protein and hydrophobic groups on the matrix serves as the basis for separating a protein from impurities including fragments and aggregates of the subject protein, other proteins or other protein fragments and other contaminants such as residual cellular impurities from other purification steps. The solid or stationary phase comprises a base matrix or support such as a cross-linked agarose, silica or synthetic copolymer material to which hydrophobic ligands are attached. The solid phase can be a porous particle, nonporous particle, membrane, or monolith.

MMC differs from cation exchange, anion exchange, hydrophobic interaction, etc. chromatography as the resin (or support) is capable two or more mechanisms simultaneously. So while a MMC separation may include a cation exchange or anion exchange component, it is well understood in the art to be a different form of chromatography separation. Thus, in some embodiments, the methods disclosed herein comprise a MMC step (which may include a cation and/or anion exchange component), but do not comprise cation and/or anion exchange chromatography. Specifically contemplated MMC supports include Capto® MMC, GE Capto® Adhere, HEA HyperCel™, PPA HyperCel™, MBI HyperCel™, MEP HyperCel™, Blue Trisacryl M, CFT™ Ceramic Fluoroapatite, CHT™ Ceramic Hydroxyapatite, and ABx resin.

In some embodiments, the absorption of the protein onto the MMC column increases as the salt concentration increases in the mobile phase and the elution is achieved by decreasing the salt concentration of the eluant or by changing the elution pH or both. (Optimization of loading conditions on Capto adhere using design of experiments, GEHC Application Note: 28-9078-89). A feed protein preparation before the MMC purification is called "Load Conditioning"

which refers to mixing high salt solution(s) and high concentration of buffer(s) to prepare the MMC "load" to be loaded onto the column. Generally, salt conditions in the "load" are adjusted to individual proteins. Salt concentrations of between about 0.1 M and about 0.5 M NaCl are useful for decreasing the amount of HMW species using MMC columns. In some cases, a high concentration of salt, 5 M NaCl for example, is used to adjust the feed salt concentration and a high concentration of buffer, 2 M Tris for example, is used to prepare the MMC load.

As used herein, the term "buffer" or "buffered solution" refers to solutions which resist changes in pH by the action of its conjugate acid-base range. Buffer solutions suitable for use with MMC include, but are not limited to, NaCl, KCl, $Na_2SO_4$, $K_2SO_4$, $NaNO_3$, $KNO_3$. The buffer solutions can further include buffer species. Examples of buffers that control pH at ranges of about pH 5 to about pH 9, and useful in the MMC step as disclosed herein, include N-Methylpiperazine, Piperazine, L-Histidine, 2-Amino-2-hydroxymethyl-propane-1,3-diol (Tris), bis-Tris, bis-Tris propane, Triethanolamine, T4-(2-hydroxyethyl)-1-piperazineethanesulfonic acid (HEPES), piperazine-N,N'-bis(2-ethanesulfonic acid) (PIPES), 3-(N-morpholino) propanesulfonic acid (MOPS) and other organic base buffers, and combinations of these. Buffer counter ions include chloride, sulfate, acetate. As used herein the term "loading buffer" or "equilibrium buffer" refers to the buffer containing the salt or salts which is mixed with the protein sample for loading the protein sample onto the MMC column. This buffer is also used to equilibrate the column before loading, and to wash to column after loading. The "elution buffer" refers to the buffer used to elute the protein from the column. As used herein, the term "solution" refers to either a buffered or a non-buffered solution, including water.

A specifically contemplated buffer solution is 175 mM Tris-HCl, 75 mM NaCl, pH 7.10, which can provide a sufficient buffering capacity and conductivity to facilitate the protein and HMW species binding. The NaCl concentration range can be about 75 mM to about 200 mM, or more specifically, about 85 mM, or 120 mM, or 150 mM, or 170 mM, or 180 mM. The buffer pH can be 6.9 to 7.3, and in some cases about ±0.1 to 3 or ±0.1 to 2 pH unit of the pI of the protein being purified.

In some embodiments, the MMC support exploits a combination of anion exchange and hydrophobic interaction functionalities. Commercial examples of such supports include, but are not limited to, MEP-Hypercel™ and Capto Adhere™.

In some embodiments, the MMC support exploits a combination of cation exchange and hydrophilic interaction functionalities. Commercial examples of such supports include, but are not limited to, Capto-MMC™.

In some embodiments, the MMC support exploits a combination of cation exchange, anion exchange, and hydrophobic interaction functionalities. Commercial examples of such supports include, but are not limited to, ABx™.

In some embodiments, the MMC support exploits a combination of anion exchange and hydrophobic interaction functionalities with potential for hydrogen bonding and pi-pi bonding. Commercial examples of such supports include, but are not limited to, Capto-Adhere™.

In some embodiments, the MMC support exploits a combination of cation exchange and hydrophobic interaction functionalities with potential for hydrogen bonding and pi-pi bonding. Commercial examples of such supports include, but are not limited to, Capto-MMC™.

Other non-commercial mixed mode media include, for example, mixed-mode chromatography support exploiting a combination of cation or anion exchange with hydrophobic interaction functionalities in the same ligand, or in a combination of ligands. Some examples of such ligands are described in, e.g., U.S. Pat. Nos. 7,008,542; 6,498,236; and 5,945,520.

In some embodiments, an exemplary protocol for using an MMC column is generally as follows. The column is first equilibrated with several column volumes of Tris HCl and sodium chloride, for example 175 mM Tris HCl and 75 mM NaCl at a pH of about 7.1. The conditioned protein sample is loaded onto the column with a buffer solution, which can be the same buffer solution as used in the equilibration step (e.g., 175 mM Tris HCl and 75 mM NaCl at a pH of about 7.1). The protein is then flowed through the column with decreased amounts of HMW species and/or high mannose species, typically within about 4 column volumes of the elution buffer, which in some cases can be the same buffer solution as the equilibration buffer solution.

In some embodiments, the MMC step is performed in a "bind/elute" mode. The protein sample is applied to the MMC support under conditions that permit the binding of protein and contaminants, with fractionation of the protein being achieved subsequently by changing the conditions such that the protein is eluted while contaminants (such as high molecular weight species) remain bound to the support. More specifically, both high molecular weight species and protein can bind to the column. In some embodiments, protein sample application is followed with a wash buffer, sometimes of the same composition as the equilibration buffer. This removes unretained contaminants from the column. The protein is then eluted from the column under conditions that leave high molecular weight species bound to the column. Retained high molecular weight species can optionally be removed from the column with an appropriate cleaning buffer.

In some embodiments, the MMC step is performed in a "flow through" mode. Flow-through mode conditions can be developed depending on the specific protein desired. Without intending to limit the scope of the invention, the following description is provided as a guide for developing flow-through conditions as desired for a particular protein. For example, phosphate, sodium chloride, other salts, or a combination thereof, is tested at a variety of concentrations and conditions (e.g., temperature, pH, conductivity, buffer selection, buffer concentrations, flow rate, etc.) to identify conditions at which the protein or high molecular weight species elute. The appropriate concentration of salts and conditions is identified at which the protein flows through but the high molecular weight species remain bound to the column.

Various parameters can be modified to improve separation and purification of the protein of interest using the MMC step. Parameters include protein loading, temperature of operation, elution buffer choice, conductivity of the protein being loaded onto the column, bed heights (column height), linear velocities, and pH. Protein loading can be about 50 to about 200 g/L, about 55 to about 85 g/L, about 60 to about 80 g/L, about 65 to about 75 g/L, about 100 to about 200 g/L, about 100 to about 150 g/L, about 125 to about 175 g/L, about 150 to about 200 g/L, or about 90 to about 140 g/L. Temperature of operation can be about 15° C. to about 25° C., or about 18° C. to about 22° C. The column height can be about 15 cm to about 35 cm, or about 20 cm to about 30 cm, or about 23 cm to about 27 cm. The linear velocity can be about 100 cm/hr to about 500 cm/hr, or about 120 cm/hr to about 170 cm/hr, about 125 cm/hr to about 165 cm/hr, or about 135 cm/hr to about 160 cm/hr. The pH can be about 5 to about 9, about 5 to about 7, about 7 to about 9, about 6 to about 8, about 5.5 to about 8.5, about 6.5 to about 8.5, about 5 to about 6, about 8 to about 9, about 7 to about 8, about 7 to about 7.5, or about 7.5 to about 8. In various cases, the pH is ±2 pH units of the pI of the protein of interest, or ±1 pH unit of the pI of the protein of interest, or ±0.5 pH units of the pI of the protein of interest. The conductivity of the protein being loaded onto the column can be about 10 to about 50 mS/cm, about 10 to about 20 mS/cm, about 15 to about 25 mS/cm, about 10 to about 30 mS/cm, about 10 to about 40 mS/cm, about 20 to about 50 mS/cm, about 30 to about 50 mS/cm, about 40 to about 50 mS/cm, about 20 to about 30 mS/cm, about 30 to about 40 mS/cm, or about 15 to about 30 mS/cm. In some cases, the buffer used in the elution of the protein is 175 mM Tris HCl and 75 mM NaCl at a pH of about 7.1.

Experiments performed in support of the present invention indicate that the MMC step can remove significant amounts of HMW species from the protein sample. The amount of HMW species present after the MMC step may be, for example, about 5% to about 20%, or 20% or less, 15% or less, 10% or less, or 5% or less (by weight) than the amount present before the MMC step. In various embodiments, the amount of HMW species present are about 5% to about 15%, about 5% to about 14%, about 7% to about 14%, about 7% to about 12%, or about 8% to about 11%. The amount of HMW species is reduced by at least about 40%, at least 45%, at least 50%, at least 55%, at least 60%, at least 65%, or at least 70%, compared to the amount of HMW species present in the protein sample prior to being subject to MMC. In various embodiments, the HMW species are decreased by about 45% to about 75%, about 40% to about 70%, about 45% to about 65%, or about 45% to about 60%, compared to the amount of HMW species prior to the MMC step. The amount of HMW species in a protein sample may be determined, e.g., using size exclusion HPLC and expressed as a % weight or molar ratio HMW species relative to the total protein of interest in the sample. This method can detect the amount of HMW species in a protein sample with an accuracy down to 0.1%.

High mannose species may be decreased in the protein sample by being subjected to MMC. The amount of high mannose species is reduced by at least about 5%, at least about 10%, at least 15%, at least 20%, at least 25%, or at least 30%, compared to the amount of high mannose species present in the protein sample prior to being subject to MMC. In various embodiments, the high mannose species are decreased by about 5% to about 25%, about 5% to about 20%, about 5% to about 15%, or about 5% to about 10%, compared to the amount of high mannose species prior to the MMC step. The percent reduction may be determined, e.g., using size exclusion HPLC and expressed as a % weight or molar ratio high mannose species relative to the total protein of interest in the sample. This method can detect the amount of high mannose species in a protein sample with an accuracy down to 0.1%.

Hydrophobic Interaction Chromatography

Although the hydrophobic interaction chromatography (HIC) step may be performed before or after the MMC step, Experiments performed in support of the present invention and described herein employed an arrangement whereby the HIC step was performed after a MMC step, i.e., the eluate from the MMC step (containing the protein of interest), is used in the loading for the HIC step. Although high molecular weight species are typically reduced in a protein sample subjected to MMC, some high molecular weight species may still be present in the protein sample after the MMC step. The HIC step may thus be used to remove even more of the HMW species from the protein sample. For example, the amount of HMW species present after the HIC step may be 1% or less, 0.5% or less, or 0.2% or less by weight than was present in the sample before the HIC step. In various embodiments, the amount of HMW species present are about 0.01% to about 1%, about 0.01% to about 0.8%, about 0.05% to about 0.5%, about 0.05% to about 0.3%, or about 0.05% to about 0.2%, based upon total amount of protein of interest.

As outlined above, the HIC step can remove even more of the high mannose species from the protein sample. The amount of high mannose species is decreased after the HIC step by about 10% to about 40%, compared to the amount of high mannose species present prior to MMC step. The HIC step removes even more of the high mannose species from the protein sample. In various embodiments, the high mannose species are decreased by about 10% to about 35%, about 10% to about 30%, about 10% to about 25%, or about 10% to about 20%, compared to the amount of high mannose species prior to the MMC step.

HIC relies on separation of proteins on the basis of hydrophobic interactions between non-polar regions on the surface of proteins and insoluble, immobilized hydrophobic groups on the matrix. The absorption increases with high salt concentration in the mobile phase and the elution is achieved by decreasing the salt concentration of the eluant (Fausnaugh et al. J Chromatogr 359, 131-146 (1986)). A protein preparation at any stage of purification is "conditioned" in preparation for HIC by mixing with high salt buffers to prepare the HIC "load" to be loaded onto the column. Generally, salt conditions are adjusted to individual proteins. Generally, requirements of between about 0.7 and about 2 M ammonium sulfate and between about 1.0 and 4.0 M NaCl salt concentration has been considered as useful for purifying proteins using HIC columns. The practice was to add a high concentration of salt to a low concentration buffer solution, such as, for example, 1.4 M $NH_4SO_4$ added to a 0.024 M phosphate buffer for the purification of monoclonal antibodies at pH 7.2 (Nau et al. BioChromatography 62 (5), 62-74 (1990)); or 1.7 M ammonium sulfate in 50 mM $NaPO_4$ for purifying yeast cell surface proteins (Singleton et al., J. Bacteriology 183 (12) 3582-3588 (2001)). In some cases, an intermediate concentration of a buffering salt in combination with an intermediate concentration of a second buffering salt, or in combination with an intermediate concentration of a second non-buffering salt can be used to achieve increased dynamic capacity. In various cases, the protein from the MMC step is loaded onto the HIC column using MOPS (3-(N-morpholino)propanesulfonic acid) and ammonium sulfate. The MOPS can be at a concentration of about 20 mM. The ammonium sulfate can be at a concentration of about 1.1 M.

As used herein the term "dynamic capacity" of a separation column such as a hydrophobic interaction chromatography column refers to the maximum amount of protein in solution which can be loaded onto a column without significant breakthrough or leakage of the protein into the solution phase of a column before elution. More formally, K' (capacity factor)=moles of solute in stationary phase divided by moles of solute in mobile phase=Vr−Vo/Vo, where Vr is the volume of the retained solute and Vo is the volume of unretarded solute. Practically, dynamic capacity of a given HIC column is determined by measuring the amount of protein loaded onto the column, and determining the resin load which is mg protein/column volume (mg/ml-r). The amount of protein leaving the column in the solution phase after the column is loaded ("breakthrough") but before elution begins can then be measured by collecting fractions during the loading process and first wash with equilibrium buffer. The load at which no significant breakthrough occurs is the dynamic capacity of the protein for those conditions.

It has also been recognized that increasing salt concentrations can increase the "dynamic capacity" of a column without "breakthrough" or loss of protein to the solution phase before elution. At the same time, high salt can be detrimental to protein stability. High salt increases the viscosity of a solution, can result in increased formation of aggregated species, can result in protein loss due to dilution and filtration of the protein after elution from the column, and can lead to reduced purity (Queiroz et al., J. Biotechnology 87:143-159 (2001), Sofer et al., Process Chromatography, Academic Press (1999)).

As used herein, the term "hydrophobic interaction chromatography (HIC)" column refers to a column containing a stationary phase or resin and a mobile or solution phase in which the hydrophobic interaction between a protein and hydrophobic groups on the matrix serves as the basis for separating a protein from impurities including fragments and aggregates of the subject protein, other proteins or other protein fragments and other contaminants such as cell debris, or residual impurities from other purification steps. The stationary phase comprises a base matrix or support such as a cross-linked agarose, silica or synthetic copolymer material to which hydrophobic ligands are attached.

As used herein, the term "buffer" or "buffered solution" refers to solutions which resist changes in pH by the action of its conjugate acid-base range. Examples of buffers that control pH at ranges of about pH 5 to about pH 7 include citrate, phosphate, and acetate, and other mineral acid or organic acid buffers, and combinations of these. Salt cations include sodium, ammonium, and potassium. As used herein the term "loading buffer" or "equilibrium buffer" refers to the buffer containing the salt or salts which is mixed with the protein preparation for loading the protein preparation onto the HIC column. This buffer is also used to equilibrate the column before loading, and to wash to column after loading the protein. The "elution buffer" refers to the buffer used to elute the protein from the column. As used herein, the term "solution" refers to either a buffered or a non-buffered solution, including water.

As used herein, the term "lyotropic" refers to the influence of different salts on hydrophobic interactions, more specifically the degree to which an anion increases the salting out effect on proteins, or for cations, increases the salting-in effect on proteins according to the Hofmeister series for precipitation of proteins from aqueous solutions (Queiroz et al. J. Biotechnology 87: 143-159 (2001), Palman et al. J. Chromatography 131, 99-108 (1977), Roe et al. Protein Purification Methods: A Practical Approach. IRL Press Oxford, pp. 221-232 (1989)). The series for anions in order of decreasing salting-out effect is: $PO_4^{3-}>SO_4^{2-}\rightarrow CH_3COO^->Cl^->Br^->NO_3^->ClO_4^->I^->SCN^-$, while the series for cations in order of increasing salting-in effect: $NH_4^+<Rb^+<K^+<Na^+<Li^+<Mg^{2+}<Ca^{2+}<Ba^{2+}$ (Queiroz et al., supra). Combining two different salts having different lyotrophic values with a protein preparation can allow more protein to be loaded onto a column with no or negligible breakthrough compared with higher salt concentrations of each single salt.

The ions at the beginning of the HIC series promote hydrophobic interactions and protein precipitation or salting out effects, and are called antichaotropic (Queiroz et al., supra). They are considered to be water structuring, whereas the ions at the end of the series are salting-in or chaotropic ions, and randomize the structure of water and tend to decrease the strength of hydrophobic interactions and result in denaturation (Porath et al., Biotechnol Prog 3: 14-21 (1987)). The tendency to promote hydrophobic interactions is the same tendency which promotes protein precipitation, and thus determining the salt concentration which causes a particular protein to begin to precipitate is a means of determining an appropriate concentration of that salt to use in an HIC column.

In various embodiments, a first salt and a second salt are selected which have differing lyotropic values. This combination of salts acts together to increase the dynamic capacity of the HIC column for a particular protein. Each salt in combination can be provided at a lower concentration that the concentration of the salt alone to achieve a higher dynamic capacity for a protein compared with the dynamic capacity using a single salt. In various cases, at least one salt has a buffering capacity at the desired pH.

The appropriate concentrations of the salts are determined for a particular protein by generating precipitation curves for individual salts, then for combined salts. On the basis of individual salt precipitation curves, precipitation curves for combinations of salts are generated by holding one salt concentration constant, and varying the concentration of the second salt. Then the concentration of the second salt is held constant, and the concentration of the first salt is varied. From these two-salt precipitation curves, concentrations of salts useful for increasing the dynamic capacity of an HIC column can be determined. See, e.g., U.S. Pat. No. 8,273,707, in which the concentrations of two salt combinations are determined using precipitation curves for each particular protein. In addition, the salt concentrations can be optimized in order to confer additional stability on a protein at room temperature, for example, or to limit aggregate formation. The dynamic capacity of a hydrophobic interaction chromatography column can be maximized for a particular protein by selecting a combination of concentrations for a first and second salt having different lyotropic values by generating a series of precipitation curves for the salts alone, and then in combination holding a each salt constant while varying the second.

The salts for use in the HIC step can be selected from those having a buffering capacity at the pH at which the protein to be purified is stable. In some embodiments, salt combinations are chosen with a buffering capacity at between about pH 5 to about 7. These include, for example, citrate, phosphate, and acetate, and other mineral acid or organic acid buffers, and combinations of these. A second salt is selected from a salt which may or may not buffer at the desired pH, and can be added to the buffered solution, such as ammonium or sodium sulfate. Cations are selected from those which are non-toxic and non-denaturing. Preferred cations according to the present invention are sodium, potassium, and ammonium, with sodium being the most preferred for manufacturing purposes. Preferred salts for purifying proteins according to the present invention include combinations of sodium citrate, sodium phosphate, sodium acetate, and sodium sulfate.

The concentration of the salt(s) used in the HIC step will depend on the characteristics of the particular salts. In various embodiments, the salts are used at concentrations from about 0.1 M to about 1.0 M in the final concentration of the mixture of salt solution and protein preparation depending on the salt and protein, in another embodiment is in the range between about 0.3 M and about 0.7 M. The pH of the buffered solution may be varied depending on requirements of the protein separation. In some embodiments, the pH varies between about pH 5 to about pH 7, about 5.5 to about 7.5, about 6 to about 7.5, about 6.5 to about 8, about 6.5 to about 7.3, about 7 to about 7.5, or about 7 to about 8.

Any type of HIC stationary phase can be used in the HIC step. Stationary phases vary in terms of ligand, ligand chain length, ligand density, and type of matrix or support. Ligands used for HIC include linear chain alkanes with and without an amino group, aromatic groups such as phenyl and N-alkane ligands including methyl, ethyl, propyl, butyl, pentyl, hexyl, heptyl and octyl (Queiroz et al, supra). Many types of HIC columns are available commercially. These include, but are not limited to, Tosoh Phenyl 650S, Tosoh Butyl 650S, Tosoh Hexyl 650C, GE Butyl High Performance, SEPHAROSE™ columns such as Phenyl SEPHAROSE™ (Pharmacia LCK Biotechnology, AB, Sweden), Octyl SEPHAROSE™ High Performance column (Pharmacia LKB Biotechnology, AB, Sweden), FAST FLOW™ column with low or high substitution (Pharmacia LKB Biotechnology, AB, Sweden); GE Phenyl 6 Fast Flow High Sub, GE Phenyl 6 Fast Flow Low Sub, GE Butyl 4 Fast Flow, GE Butyl-S 6 Fast Flow; GE Phenyl High Performance, GE Octyl 4 Fast Flow, FRACTOGEL™ EMD Propyl or FRACTOGEL™, EMD Phenyl columns (E. Merck, Germany); Phenyl HP column (GE Healthcare Life Sciences); MACRO-PREP™ Methyl or MACRO-PREP™ t-Butyl Supports (Bio-Rad, Calif.); WP HI-Propyl ($C_3$)™ column (J. T. Baker, N.J.); and TOYOPEARL™ ether, phenyl or butyl columns (TosoHaas, Pa.). In various cases, the HIC stationary phase is selected from GE Phenyl High Performance; GE Octyl 4 Fast Flow; EMD Fractogel Phenyl; Tosoh Phenyl 650S; Tosoh Butyl 650S; Tosoh Hexyl 650C; GE Butyl High Performance; GE Phenyl 6 Fast Flow High Sub; GE Phenyl 6 Fast Flow Low Sub; GE Butyl 4 Fast Flow; and GE Butyl-6 Fast Flow. In some embodiments, the HIC stationary phase is Phenyl HP.

The mobile phase of HIC can be a two salt solution. Commercial application processes for purifying large quantities of proteins require that the exact ion concentrations of the two salt solution be constant and consistent. Therefore, the adjustment of the dissolved salt solution is made with the acid form of the salt, such as citric acid mixed with citrate to get an exact ion concentration. At least one salt in the two salt solution can have a buffering effect at the pH at which the protein to be purified is stable. In various embodiments, the buffering capacity of at least one salt is between pH 5 to about pH 7.

The protocol for using an HIC column is generally as follows. The column is first regenerated with several column volumes of sodium hydroxide, 0.5 N NaOH, for example, and then washed with water. The column is then equilibrated with several column volumes of equilibration buffer, which is the same buffer containing the protein preparation for loading onto the column. The protein preparation is prepared by "conditioning" or mixing with the buffered solution (in some cases the two salt solution). Generally the salt solution is added slowly to avoid localized protein destabilization. Next, the protein/buffered salt solution mixture is loaded onto the column, and the column washed with several column volumes of equilibrium buffer. The HIC column is then eluted. Elution can be accomplished by decreasing the salt concentration of the buffer using a salt gradient or isocratic elution. The gradient or step starts at equilibrium buffer salt concentration, and is then reduced as a continuous gradient, or as discrete steps of successively lower concentrations. The elution generally concludes with washing the column with a solution such as a no-salt buffer, such as low ionic strength MES buffer, or a MOPS buffer, for example. Elution of the subject protein can also be accomplished by changing the polarity of the solvent, and by adding detergents to the buffer. The protein when purified can be diafiltered or diluted to remove any remaining excess salts.

In some embodiments, the HIC step is performed in a "bind/elute" mode. The protein sample is applied to the HIC support under conditions that permit the binding of protein and contaminants, with fractionation of the protein being achieved subsequently by changing the conditions such that the protein is eluted while contaminants (such as high molecular weight species) remain bound to the support. More specifically, both high molecular weight species and protein can bind to the column. In some embodiments, protein sample application is followed with a wash buffer, sometimes of the same composition as the equilibration buffer. This removes unretained contaminants from the column. The protein is then eluted from the column under conditions that leave high molecular weight species bound to the column. Retained high molecular weight species can optionally be removed from the column with an appropriate cleaning buffer.

In some embodiments, the HIC step is performed in a "flow through" mode. Flow-through mode conditions can be developed depending on the specific protein desired. Without intending to limit the scope of the invention, the following description is provided as a guide for developing flow-through conditions (e.g. temperature, pH, conductivity, buffer selection, buffer concentration, etc.) as desired for a particular protein. For example, phosphate, sodium chloride, other salts, or a combination thereof, is tested at a variety of concentrations and conditions to identify conditions at which the protein or high molecular weight species elute. The appropriate concentration of salts and conditions is identified at which the protein flows through but the high molecular weight species remain bound to the column.

Various parameters can be modified to improve separation and purification of the protein of interest using the HIC step. Parameters include protein loading, temperature of operation, column volume gradient, bed heights (column height), linear velocities, and pH. Protein loading can be about 1 to about 45 g/L, about 1 to about 40 g/L, about 1 to about 30 g/L, about 10 to about 45 g/L, about 10 to about 35 g/L, about 5 to about 45 g/L, about 5 to about 20 g/L, about 5 to about 15 g/L, about 15 to about 45 g/L, about 5 to about 15 g/L, about 5 to about 30 g/L, about 25 to about 45 g/L, about 30 to about 40 g/L, or about 32 to about 37 g/L. Temperature of operation can be about 0° C. to about 40° C., about 0° C. to about 30° C., about 10° C. to about 30° C., about 0° C. to about 20° C., about 10° C. to about 40° C., about 10° C. to about 25° C., about 0° C. to about 25° C., about 15° C. to about 25° C., or about 18° C. to about 22° C. The protein can be eluted using about 5 to about 30 column volume gradient, about 10 to about 30 column volume gradient, about 5 to about 20 column volume gradient, about 20 to about 30 column volume gradient, about 10 to about 20 column volume gradient, or about 10 to about 15 column volumes. The column height can be about 5 to about 30 cm, about 10 to about 30 cm, about 15 to about 25 cm, about 5 to about 20 cm, about 10 cm to about 20 cm, or about 10 cm to about 15 cm, or about 13 cm to about 17 cm. The linear velocity can be about 60 cm/hr to about 120 cm/hr, or about 70 cm/hr to about 110 cm/hr, about 80 cm/hr to about 100 cm/hr, or about 85 cm/hr to about 95 cm/hr. The pH can be about 5 to about 9, about 5 to about 7, about 7 to about 9, about 6 to about 8, about 5.5 to about 8.5, about 6.5 to about 8.5, about 5 to about 6, about 8 to about 9, about 7 to about 8, about 7 to about 7.5, or about 7.5 to about 8. In various cases, the loading phase is performed at a different pH than the elusion phase pH. In some cases, the loading phase is at a lower pH than the elution phase pH, while in other cases the loading phase is at a higher pH than the elution phase pH. The difference can be ±about 1.5 pH unit, ±about 1 pH unit, ±about 0.75 pH unit, ±about 0.5 pH unit, ±about 0.25 pH unit, or ±about 0.1 pH unit. In some cases, the buffers used in the gradient are (a) 1.1 M ammonium sulfate with 20 mM MOPS at pH 7 and (b) 20 mM MOPS at pH 7.

Proteins

Generally, the methods disclosed herein can be used in the removal of high molecular weight species and to reduce high mannose species from preparations (or samples) of recombinant proteins. Recombinant proteins are proteins produced by the process of genetic engineering. The term "genetic engineering" refers to any recombinant DNA or RNA method used to create a host cell that expresses a gene at elevated levels, at lowered levels, and/or expresses a mutant form of the gene, or expresses a modified gene product. For example, a cell that has been transfected, transformed or transduced with a recombinant polynucleotide molecule, and thereby altered so as to cause the cell to alter expression of a desired protein. Methods and vectors for genetically engineering cells and/or cell lines to express a protein of interest are well known to those skilled in the art; for example, various techniques are illustrated in Current Protocols in Molecular Biology, Ausubel et al., eds. (Wiley & Sons, New York, 1988, and quarterly updates) and Sambrook et al., Molecular Cloning: A Laboratory Manual (Cold Spring Laboratory Press, 1989).

The proteins can be glycosylated. Specifically, proteins that are secreted by fungal cell systems (e.g., yeast, filamentous fungi) and mammalian cell systems will be glycosylated. The proteins can be secreted by mammalian production cells adapted to grow in cell culture. Examples of such cells commonly used in the industry are CHO, VERO, BHK, HeLa, CV1 (including Cos), MDCK, 293, 3T3, myeloma cell lines (especially murine), PC12 and WI38 cells. Particularly preferred host cells are Chinese hamster ovary (CHO) cells, which are widely used for the production of several complex recombinant proteins, e.g. cytokines, clotting factors, and antibodies (Brasel et al., 1996, Blood 88:2004-2012; Kaufman et al., 1988, J. Biol Chem 263: 6352-6362; McKinnon et al., 1991, J Mol Endocrinol 6:231-239; Wood et al., 1990, J. Immunol 145:3011-3016). The dihydrofolate reductase (DHFR)-deficient mutant cell line (Urlaub et al., 1980, Proc Natl Acad Sci USA 77:4216-4220), DXB11 and DG-44, are the CHO host cell lines of choice because the efficient DHFR selectable and amplifiable gene expression system allows high level recombinant protein expression in these cells (Kaufman R. J., 1990, Meth Enzymol 185:527-566). In addition, these cells are easy to manipulate as adherent or suspension cultures and exhibit relatively good genetic stability. CHO cells and recombinant proteins expressed in them have been extensively characterized and have been approved for use in clinical manufacturing by regulatory agencies.

The methods disclosed herein are also generally applicable to proteins that have an Fc domain, and another domain (e.g., antibodies, and Fc fusion proteins). The recombinant proteins or polypeptide of the invention include immunoglobulin molecules or portions thereof, and chimeric antibodies (e.g., an antibody having a human constant region coupled to a murine antigen binding region) or fragments thereof. Numerous techniques are known by which DNA encoding immunoglobulin molecules can be manipulated to yield DNAs capable of encoding recombinant proteins such as single chain antibodies, antibodies with enhanced affinity, or other antibody-based polypeptides (see, for example, Larrick et al., 1989, Biotechnology 7:934-938; Reichmann et al., 1988, Nature 332:323-327; Roberts et al., 1987, Nature 328:731-734; Verhoeyen et al., 1988, Science 239:1534-1536; Chaudhary et al., 1989, Nature 339:394-397). Preparations of fully human antibodies (such as are prepared using transgenic animals, and optionally further modified in vitro), as well as humanized antibodies, can also be prepared or purified using the methods of the invention. The term humanized antibody also encompasses single chain antibodies. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. The method of the invention may also be used during the preparation of conjugates comprising an antibody and a cytotoxic or luminescent substance. Such substances include: maytansine derivatives (such as DM1); enterotoxins (such as a Staphlyococcal enterotoxin); iodine isotopes (such as iodine-125); technium isotopes (such as Tc-99m); cyanine fluorochromes (such as Cy5.5.18); and ribosome-inactivating proteins (such as bouganin, gelonin, or saporin-S6).

Examples of antibodies or antibody/cytotoxin or antibody/luminophore conjugates contemplated include those that recognize any one or combination of the above-described proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-la, IL-1β, IL-4, IL-5, IL-8, IL-10, IL-2 receptor, IL-4 receptor, IL-6 receptor, IL-13 receptor, IL-18 receptor subunits, TNFR (p55 and p75), PDGF-β, VEGF, TGF, TGF-β2, TGF-β1, EGF receptor, VEGF receptor, CS complement, IgE, tumor antigen CA125, tumor antigen MUC1, PEM antigen, LCG (which is a gene product that is expressed in association with lung cancer), HER-2, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), α-fetoprotein (AFP), tumor necrosis factor (TNF), CTLA-4 (which is a cytotoxic T lymphocyte-associated antigen), Fc-γ-1 receptor, HLA-DR 10β, HLA-DR antigen, L-selectin, IFN-γ, Respiratory Syncitial Virus, human imillimolarunodeficiency virus (HIV), hepatitis B virus (HBV), *Streptococcus mutans*, and *Staphlycoccus aureus*. Specifically contemplated antibodies include infliximab, enteracept, anakinra, adalimumab, certolizumab pegol and golimimab.

In some cases, the protein or polypeptides is a protein-based drug, also known as biologics. Preferably, the proteins are expressed as extracellular products. Proteins that can be prepared or purified using the methods of the invention include but are not limited to a flt3 ligand (as described in WO 94/28391, which is incorporated by reference herein in its entirety), a CD40 ligand (as described in U.S. Pat. No. 6,087,329, which is incorporated by reference herein in its entirety), erythropoeitin, thrombopoeitin, calcitonin, Fas ligand, ligand for receptor activator of NF-kappa B (RANKL), tumor necrosis factor (TNF)-related apoptosis-inducing ligand (TRAIL, as described in WO 97/01633, which is incorporated by reference herein in its entirety), thymic stroma-derived lymphopoietin, granulocyte colony stimulating factor, granulocyte-macrophage colony stimulating factor (GM-CSF, as described in Australian Patent No. 588819, which is incorporated by reference herein in its entirety), mast cell growth factor, stem cell growth factor, epidermal growth factor, RANTES, growth hormone, insulin, insulinotropin, insulin-like growth factors, parathyroid hormone, interferons, nerve growth factors, glucagon, interleukins 1 through 18, colony stimulating factors, lymphotoxin-β tumor necrosis factor (TNF), leukemia inhibitory factor, oncostatin-M, and various ligands for cell surface molecules ELK and Hek (such as the ligands for eph-related kinases or LERKS). Descriptions of proteins that can be purified according to the inventive methods may be found in, for example, Human Cytokines: Handbook for Basic and Clinical Research, Vol. II (Aggarwal and Gutterman, eds. Blackwell Sciences, Cambridge, Mass., 1998); Growth Factors: A Practical Approach (McKay and Leigh, eds., Oxford University Press Inc., New York, 1993); and The Cytokine Handbook (A. W. Thompson, ed., Academic Press, San Diego, Calif., 1991).

Preparations of the receptors, especially soluble forms of the receptors, for any of the aforementioned proteins can also be improved using the inventive methods, including both forms of TNFR (referred to as p55 and p'75), Interleukin-1 receptors types I and II (as described in EP 0 460 846, U.S. Pat. No. 4,968,607, and U.S. Pat. No. 5,767,064, which are incorporated by reference herein in their entirety), Interleukin-2 receptor, Interleukin-4 receptor (as described in EP 0 367 566 and U.S. Pat. No. 5,856,296, which are incorporated by reference herein in their entirety), Interleukin-15 receptor, Interleukin-17 receptor, Interleukin-18 receptor, granulocyte-macrophage colony stimulating factor receptor, granulocyte colony stimulating factor receptor, receptors for oncostatin-M and leukemia inhibitory factor, receptor activator of NF-kappa B (RANK, as described in U.S. Pat. No. 6,271,349, which is incorporated by reference herein in its entirety), receptors for TRAIL (including TRAIL receptors 1, 2, 3, and 4), and receptors that comprise death domains, such as Fas or Apoptosis-Inducing Receptor (AIR).

Other proteins or polypeptides that can be purified or prepared by the disclosed methods include cluster of differentiation antigens (referred to as CD proteins), for example, those disclosed in Leukocyte Typing VI (Proceedings of the VIth International Workshop and Conference; Kishimoto, Kikutani et al., eds.; Kobe, Japan, 1996), or CD molecules disclosed in subsequent workshops. Examples of such molecules include CD27, CD30, CD39, CD40; and ligands thereto (CD27 ligand, CD30 ligand and CD40 ligand). Several of these are members of the TNF receptor family, which also includes 41BB and OX40; the ligands are often members of the TNF family (as are 41BB ligand and OX40 ligand); accordingly, members of the TNF and TNFR families can also be produced using the present invention.

Proteins that are enzymatically active can also be prepared or purified using the disclosed methods. Examples include metalloproteinase-disintegrin family members, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, TNF-alpha Converting Enzyme, and numerous other enzymes. Ligands for enzymatically active proteins can also be expressed by applying the instant invention.

Preparations of various fusion proteins can also be purified or prepared by the disclosed methods. Examples of such fusion proteins include proteins expressed as a fusion with a portion of an immunoglobulin molecule, proteins expressed as fusion proteins with a zipper moiety, and novel polyfunctional proteins such as a fusion proteins of a cytokine and a growth factor (i.e., GM-CSF and IL-3, MGF and IL-3). WO 93/08207 and WO 96/40918 describe the preparation of various soluble oligomeric forms of a molecule referred to as CD40L, including an immunoglobulin fusion protein and a zipper fusion protein, respectively; the techniques discussed therein are applicable to other proteins. Any of the above molecules can be expressed as a fusion protein including but not limited to the extracellular domain of a cellular receptor molecule, an enzyme, a hormone, a cytokine, a portion of an immunoglobulin molecule, a zipper domain, and an epitope.

The "protein sample" may be a cell culture supernatant, cell extract, or a partially purified fraction comprising a recombinantly expressed protein or polypeptide. By "partially purified" means that some fractionation procedure, or procedures, have been carried out, but that more polypeptide species (at least 10%) than the desired protein or protein conformation is present. Protein concentration ranges include 0.1 to 20 mg/ml, more preferably from 0.5 to 15 mg/ml, and still more preferably from 1 to 10 mg/ml.

The recombinant protein or polypeptide can be prepared initially by culturing recombinant host cells under culture conditions suitable to express the polypeptide. The polypeptide can also be expressed as a product of transgenic animals, e.g., as a component of the milk of transgenic cows, goats, pigs, or sheep which are characterized by somatic or germ cells containing a nucleotide sequence encoding the polypeptide.

A "biosimilars" is a biological product that is highly similar to a reference biological product (e.g., Adalimumab) notwithstanding minor differences in clinically inactive components, and for which there are no clinically meaningful differences between the biological product and the reference product in terms of the safety, purity, and potency of the product.

Adalimumab or Biosimilar Purification

In various embodiments, a protein sample comprising adalimumab or a biosimilar thereof is subjected to MMC and to HIC. The MMC step is performed in flow through mode with Capto® Adhere resin, and the HIC step is performed in bind/elute mode with Phenyl HP resin. The MMC step is performed using the following conditions: the adalimumab sample is conditioned by adding a salt and buffer solution, to achieve the appropriate conductivity and pH of the protein sample prior to loading (e.g., using 5 M NaCl and a buffer such as 2 M Tris base to achieve a conductivity of about 15 to about 19 mS/cm and a pH of about 6.9 to about 7.3). The conditioned protein sample is then loaded, using a loading buffer, onto a Capto® Adhere column that has been equilibrated with an equilibration buffer. The adalimumab sample is then flowed through the column using a washing buffer, leading to adalimumab having a decreased amount of HMW species and/or high mannose species. The loading, equilibration and washing buffer can all having the same pH, e.g., a pH of about 7 to 7.5, or about 7.1 pH. The loading, equilibration and washing buffer can all having the same conductivity, e.g., about 15 to about 18, or about 17 mS. The MMC step can be performed once or twice prior to subjecting the adalimumab to the HIC step. The MMC column can be operated at 100-300 cm/hr linear velocity, with the adalimumab loading range of 30-120 g/L of resin. Alternatively, other salt or buffer concentration and buffer species can be used. Examples include, but are not limited to, 116 mM NaCl, 100 mM Tris-HCl; or 85 mM NaCl, 150 mM Tris-HCl; or 169 mM NaCl, 25 mM HEPES; or 169 mM NaCl, 25 mM MOPS; or 184 mM NaCl, 100 mM MOPS, with pH 7-7.2.

The HIC step is performed using the following conditions. The adalimumab sample (from the MMC step) is loaded onto the HIC Phenyl HP column, using a loading buffer, the column having been equilibrated with an equilibration buffer. The adalimumab-bound HIC column is then washed with a washing buffer. Then, the adalimumab is eluted from the resin using a elution buffer with a 0-100% gradient over 7 to 12 column volumes. The equilibration buffer and washing buffer can be the same, e.g., 20 mM MOPS and 1.1. M ammonium sulfate at a pH of about 7. The elution buffer can be a buffer having a decreased kosmotropic salt concentration to elute the protein (adalimumab). Thus, in some cases, the elution buffer has the same pH and buffer species as the washing buffer but no kosmotropic salt, e.g., 20 mM MOPS with 0 M ammonium sulfate, which is introduced to the column over a gradient of about 10-20 column volumes (from 0-100%). The adalimumab from the HIC step has reduced HMW species and/or high mannose species. Additionally, the kosmotropic salt used in the HIC step may be ammonium sulfate, sodium sulfate, potassium sulfate, or sodium citrate, optionally in a buffer at a pH of about 5 to about 8.

Alternatively, the HIC step may be performed using Tosoh Phenyl 650S, Tosoh Butyl 650S, Tosoh Hexyl 650C, GE Butyl High Performance, or a SEPHAROSE™ column such as Phenyl SEPHAROSE™ (Pharmacia LCK Biotechnology, AB, Sweden); GE Phenyl 6 Fast Flow High Sub, GE Phenyl 6 Fast Flow Low Sub, GE Butyl 4 Fast Flow, EMD Phenyl columns (E. Merck, Germany); Phenyl HP column (GE Healthcare Life Sciences); MACRO-PREP™ Methyl or MACRO-PREP™ t-Butyl Supports (Bio-Rad, Calif.); WP HI-Propyl (C$_3$)™ column (J. T. Baker, N.J.); and TOYOPEARL™ ether, phenyl or butyl columns (TosoHaas, Pa.). In various cases, the HIC stationary phase is selected from GE Phenyl High Performance; GE Octyl 4 Fast Flow; EMD Fractogel Phenyl; Tosoh Phenyl 650S; Tosoh Butyl 650S; Tosoh Hexyl 650C; GE Butyl High Performance; GE Phenyl 6 Fast Flow High Sub; GE Phenyl 6 Fast Flow Low Sub; GE Butyl 4 Fast Flow; and GE Butyl-6 Fast Flow, or Octyl SEPHAROSE™ High Performance column (Pharmacia LKB Biotechnology, AB, Sweden), FAST FLOW™ column with low or high substitution (Pharmacia LKB Biotechnology, AB, Sweden) as the resin. These resins may be used to reduce HMW and high mannose species from the adalimumab sample derived from the MMC step. The adalimumab sample is loaded onto the HIC column that had been equilibrated with an equilibration buffer, using a loading buffer. The adalimumab-bound HIC column is then washed with a washing buffer. Then, the adalimumab is eluted from the resin using a elution buffer with a 0-100% gradient over 10 to 20 column volumes. The equilibration buffer and washing buffer can be the same, e.g., 20 mM MOPS and 1.1. M ammonium sulfate at a pH of about 7. The elution buffer can be a buffer having a decreased kosmotropic salt concentration to elute the protein (adalimumab). Thus, in some cases, the elution buffer has the same pH and buffer species as the washing buffer but no kosmotropic salt, e.g., 20 mM MOPS with 0 M ammonium sulfate, which is introduced to the column over a gradient of about 10-20 column volumes (from 0-100%). The adalimumab from the HIC step has reduced HMW species and/or high mannose species. Additionally, the kosmotropic salt used in the HIC step may be sodium sulfate, potassium phosphate, or sodium citrate at a pH of 5-8.

The following examples are not intended to be limiting but only exemplary of specific embodiments of the invention.

EXAMPLES

Comparative Examples

An adalimumab sample having about 22.4% high molecular weight species was loaded onto an ion exchange column (a Q column). The protein was eluted from the ion exchange column and the amount of HMW species in the protein after elution was 21.0%.

An adalimumab sample having 10.2% high mannose species was loaded onto a Q column (ion exchange column) and eluted. After elution, the amount of high mannose species in the protein was about 10.1%.

Adalimumab samples were subjected to the following cation exchange (CEX) columns having the noted resins and eluted with a buffer at the noted pH. The reduction of HMW species was either minimal or non-existent. CMFF is Carboxymethyl FastFlow; and SPFF is Sepharose Fast Flow.

| Resin | pH | HMW % Before CEX | HMW % After CEX |
| --- | --- | --- | --- |
| CMFF | 5 | 25.1 | 21.4 |
| CMFF | 6 | 25.1 | 20.4 |
| CMFF | 7 | 25.1 | 24.8 |
| Fractogel SO3 | 5 | 23.2 | 13.9 |
| Fractogel SO4 | 6 | 23.2 | 9.5 |
| Fractogel SO5 | 7 | 23.2 | 12.8 |
| SPFF | 5 | 25.1 | 19.5 |
| SPFF | 6 | 25.1 | 18.4 |
| SPFF | 7 | 25.1 | 20.2 |

MMC-HIC Chromatography Steps

An adalimumab sample having about 19.9% high molecular weight species was loaded onto the mixed mode chromatography column having Capto Adhere (GE Healthcare) as the support. The column had a width of 40 cm, with a column height of 25±2 cm, a column volume of 31.4 L, and compression factor of 1.15. The packing buffer used was 0.1M NaCl and the protein loading was about 70 g/L, with a range of 60-80 g/L. The maximum operating pressure was 30 psi and the load pH target was 7.1±0.1. The load conductivity target was 17.0±1.0 mS/cm at 20° C.

The MMC column was equilibrated with 175 mM Tris-HCl and 75 mM NaCl at a pH of 7.1, at a linear velocity of 200 cm/hr. The column was loaded with the protein sample which had been titrated to a pH of 7.1 using 2 M Tris base and conditioned to a conductivity of 17.0 mS/cm using 5 M NaCl. Next, the loaded column was washed with a washing solution of 175 mM Tris-HCl and 75 mM NaCl at a pH of 7.1. Next, a water flush was performed, then a non-denaturing cleaning using 1 M acetic acid, followed by another water flush. Next a denaturing cleaning was performed using 1M NaOH.

Two cycles of the mixed mode chromatography were performed in flow through mode to produce an adalimumab pool having about 8.6% high molecular weight species.

The adalimumab pool from the MMC was then loaded onto a HIC column having Phenyl Sepharose High Performance (HP) support (GE Healthcare). The column was 60 cm in diameter, with a column height of 15±2 cm, a column volume of 31.4 L, and a compression factor of 1.15. The target pH of the column load was about 5.0, and the target conductivity was about 152 mS/cm. The dilution buffer used was 60 mM acetic acid and 3.0 M ammonium sulfate at a pH of 3.6.

The column was pre-equilibrated with water at a linear velocity of 90 cm/hr, then equilibrated with 20 mM MOPS, 1.1 M ammonium sulfate at pH 7, also at a linear velocity of 90 cm/hr. The protein from the MMC step was loaded onto the HIC column and washed with 20 mM MOPS, 1M ammonium sulfate at a pH of 7, at a linear velocity of 90 cm/hr. The protein was eluted using an elution buffer of 20 mM MOPS at pH 7, using a 0-100% gradient over 10 column volumes, at a linear velocity of 90 cm/hr. The column was then cleaned using water, then a denaturing cleaning using 1 M NaOH.

Two cycles of the HIC step were performed in a bind/elute mode to produce adalimumab having 0.2% high molecular weight species.

Additional runs of adalimumab samples provided similar reductions in HMW species:

| Run | Starting HMW % | HMW % After MMC | HMW % After HIC |
| --- | --- | --- | --- |
| 1 | 19.9 | 8.6 | 0.2 |
| 2 | 20.8 | 6.1 | 0.1 |
| 3 | 20.1 | 6.2 | 0.1 |
| 4 | 23.2 | 7.8 | 0.1 |
| 5 | 20.3 | 2.6 | 0.2 |
| 6 | 21.0 | 6.5 | 0.2 |

The same purification steps were run on three different adalimumab samples. Prior to subjecting the protein sample to MMC using Capto® Adhere, the adalimumab samples had 5.5%, 5.9%, and 11.9% high mannose species, respectively. After the MMC step, the amount of high mannose species was decreased to 4.4%, 4.3%, and 9.8%, respectively. After the HIC step, the amount of high mannose species in the protein sample was decreased to 4.1%, 3.9%, and 8.7%.

Additional runs of adalimumab samples provided similar decreases in high mannose species:

| Run | Starting high mannose % | High Mannose % After MMC | High Mannose % After HIC |
| --- | --- | --- | --- |
| 1 | 9.0 | 7.0 | 6.1 |
| 2 | 6.5 | 5.1 | 4.8 |
| 3 | 9.0 | 6.9 | 6.5 |
| 4 | 14.2 | 11.2 | 10.4 |
| 5 | 7.1 | 5.4 | n/d |
| 6 | 8.7 | 6.5 | 6.8 |

What is claimed:

1. A method of reducing high molecular weight (HMW) species in a protein sample comprising adalimumab or a biosimilar thereof comprising:
    (a) subjecting the protein sample to mixed mode chromatography (MMC) to form a first eluate using a washing buffer comprising Tris-HCl and NaCl, wherein the protein sample subjected to MMC has a pH of about 6.9 to about 7.3 and a conductivity at a temperature between about 18° C. and about 22° C. of about 15 to about 30 mS/cm; and
    (b) subjecting the first eluate to hydrophobic interaction chromatography (HIC) to form a second eluate using an elution buffer comprising 3-(N-morpholino) propanesulfonic acid (MOPS), wherein the second eluate has at least 40% fewer HMW species than the protein sample.

2. The method of claim 1, wherein the method does not comprise cation exchange chromatography or does not comprise anion exchange chromatography.

3. The method of claim 1, wherein the MMC is performed using a resin having a combination of functionalities selected from the group consisting of (i) anion exchange and hydrophobic interaction; (ii) cation exchange and hydrophilic interaction; (iii) cation exchange, anion exchange, and hydrophobic interaction; and (iv) anion exchange and hydrophobic interaction with potential for hydrogen bonding and pi-pi bonding.

4. The method of claim 1, wherein the HIC is performed using a Phenyl HP resin.

5. The method of claim 1, wherein the amount of HMW species in the second eluate is 1% by weight or molar ratio or less.

6. The method of claim 1, wherein the protein sample is from a cell supernatant or cell culture harvest.

7. The method of claim 1, wherein the method results in a decrease in the amount of high mannose species in the second eluate, compared to the amount of high mannose species in the protein sample, by about 10% or more.

8. The method of claim 1, wherein the washing buffer comprises about 175 mM Tris-HCl and about 75 mM NaCl at a pH about 7.1, and the elution buffer comprises about 20 mM MOPS and up to about 1.1M of a kosmotropic salt selected from ammonium sulfate, sodium sulfate, potassium sulfate, and sodium citrate, at a pH of about 7.0.

9. A method of decreasing high mannose species in a protein sample comprising adalimumab or a biosimilar thereof comprising:
    (a) subjecting the protein sample to mixed mode chromatography (MMC) to form a first eluate using a washing buffer comprising Tris-HCl and NaCl, wherein the protein sample subjected to MMC has a pH of about 6.9 to about 7.3 and a conductivity at a temperature between about 18° C. and about 22° C. of about 15 to about 30 mS/cm; and
    (b) subjecting the first eluate to hydrophobic interaction chromatography (HIC) to form a second eluate using an elution buffer comprising about 20 mM 3-(N-morpholino) propanesulfonic acid (MOPS), wherein the second eluate has at least 5% fewer high mannose species than the protein sample.

10. The method of claim 9, wherein the method does not comprise cation exchange chromatography, or does not comprise anion exchange chromatography.

11. The method of claim 9, wherein the MMC is performed using a resin having a combination of functionalities selected from the group consisting of (i) anion exchange and hydrophobic interaction; (ii) cation exchange and hydrophilic interaction; (iii) cation exchange, anion exchange, and hydrophobic interaction; and (iv) anion exchange and hydrophobic interaction with potential for hydrogen bonding and pi-pi bonding.

12. The method of claim 9, wherein the HIC is performed using a Phenyl HP resin.

13. The method of claim 9, wherein the amount of high mannose species in the second eluate is decreased by about 10% or more, compared to the amount of high mannose species in the protein sample.

14. The method of claim 9, wherein the protein sample is from a cell supernatant or cell culture harvest.

15. The method of claim 9, wherein the washing buffer comprises about 175 mM Tris-HCl and about 75 mM NaCl at a pH of about 7.1, and the elution buffer comprises about 20 mM MOPS and up to about 1.1M of a kosmotropic salt selected from ammonium sulfate, sodium sulfate, potassium sulfate, and sodium citrate, at a pH of about 7.0.

16. A method of reducing high molecular weight (HMW) species in a sample comprising adalimumab or a biosimilar thereof comprising:
    (a) subjecting the sample to mixed mode chromatography (MMC) in flow through mode to form a first eluate using a washing buffer comprising 100 mM to 175 mM Tris-HCl and about 75 mM to about 200 mM NaCl, wherein the sample subjected to MMC has a pH of about 6.9 to about 7.3 and a conductivity at a temperature between about 18° C. and about 22° C. of about 15 to about 30 mS/cm; and
    (b) subjecting the first eluate to hydrophobic interaction chromatography (HIC) in bind/elute mode to form a second eluate using an elution buffer comprising about 20 mM 3-(N-morpholino) propanesulfonic acid (MOPS), wherein the second eluate has at least 40% fewer HMW species than the sample.

17. The method of claim 16, wherein the second eluate has fewer high mannose species than the sample.

18. The method of claim 16, wherein the MMC step is performed using a resin having a combination of anion exchange and hydrophobic interaction functionalities.

19. The method of claim 18, wherein the resin has a protein loading of about 30 to about 120 g/L.

20. The method of claim 16, wherein the HIC step is performed using Phenyl HP resin.

21. The method of claim 16, wherein the amount of HMW species in the second eluate is 1% by weight or molar ratio or less.

22. The method of claim 16, wherein the method results in a decrease in the amount of high mannose species in the second eluate, compared to the amount of high mannose species in the sample, by about 10% or more.

* * * * *